United States Patent
Chen et al.

[11] Patent Number: 5,889,051
[45] Date of Patent: Mar. 30, 1999

[54] STABILIZATION OF PROSTAGLANDIN DRUG

[75] Inventors: David Chen; Rong-Jer Tsay; Hue-In Lin; Shu-Bin Lu, all of Taipei, Taiwan

[73] Assignee: Development Center for Biotechnology, Taipei, Taiwan

[21] Appl. No.: 893,265

[22] Filed: Jul. 15, 1997

[51] Int. Cl.$^6$ .................................................. A61K 31/215

[52] U.S. Cl. .......................................... 514/530; 514/964

[58] Field of Search ....................................... 514/530, 964

[56] References Cited

U.S. PATENT DOCUMENTS

| | | |
|---|---|---|
| 3,965,143 | 6/1976 | Collins et al. . |
| 4,301,146 | 11/1981 | Sanvordeker ............................. 424/80 |
| 5,232,704 | 8/1993 | Franz et al. ............................. 429/456 |

FOREIGN PATENT DOCUMENTS

| | | |
|---|---|---|
| 0410422A2 | 1/1991 | European Pat. Off. . |
| WO96/38153 | 12/1996 | WIPO . |

OTHER PUBLICATIONS

Chemical Abstracts :120:330935(C) (Collins et al), 1994.
Chemical Abstracts 110:63733a (Konishi), 1989.
Kislalioglu, M.S. et al., "Physical Characterization and Dissolution Properties of Ibuprofen: Eudragit Coprecipitates," *Journal of Pharmaceutical Sciences*, pp. 799–804, Aug. 1991.
Yuasa, Hiroshi et al., "Application of the Solid Dispersion Method to Controlled Release of Medicine. I. Controlled Release of Water Soluble Medicine by Using Solid Dispersion," *Chemical & Pharmaceutical Bulletin*, pp. 465–467, Feb. 1991.

*Primary Examiner*—Leonard Schenkman
*Attorney, Agent, or Firm*—Finnegan, Henderson, Farabow, Garrett & Dunner, L.L.P.

[57] ABSTRACT

A stable solid dispersion of prostaglandin drug, particularly Misoprostol, (±)methyl 7-[3($\alpha$)-hydroxy-2-$\beta$-(4 (RS)-4-hydroxy-4-methyl-trans-1-octen-1-yl)-oxycyclopent-1$\alpha$-yl] heptanoate, comprising ammonio methacrylate copolymers. The ammonio methacrylate copolymers comprise Eudragit RS series, Eudragit RL series, Eudragit S, Eudragit L, and the mixture thereof. The stable solid dispersion is a sustained release type.

24 Claims, 3 Drawing Sheets

5,889,051

STABILIZATION OF PROSTAGLANDIN DRUG

BACKGROUND OF THE INVENTION

1. Field of the Invention

The present invention relates to a stable solid dispersion of a prostaglandin drug, in particular, to a stable solid dosage of Misoprostol, (±) methyl 7-[3(α)-hydroxy-2-β-(4(RS)-4-hydroxy-4-methyl-trans-1-octen-1-yl)-oxycyclopent-1α-yl] heptanoate, by using ammonio methacrylate copolymers.

2. Description of the Prior Art

U.S. Pat. No. 3,965,143 discloses (±) methyl 7-[3(α)-hydroxy-2-β-(4(RS)-4-hydroxy-4-methyl-trans-1-octen-1-yl)-oxycyclopent-1α-yl]heptanoate, a potent antisecretory agent. The above compound, also known as Misoprostol, is a prostaglandin E-type drug.

Misoprostol is difficult to formulate due to its instability. The present invention provides stabilized compositions of the above anti-secretory agent. Particularly, the present invention provides a stable solid dispersion of Misoprostol for use in sustained release and a method of producing the same.

SUMMARY OF THE INVENTION

Accordingly, it is an object of the present invention to provide a stable solid dispersion of a prostaglandin drug comprising an ammonio methacrylate copolymer which is useful for stabilization.

Another object of the present invention is to provide a stable solid dispersion of Misoprostol, (±) methyl 7-[3(α)-hydroxy-2-β-(4(RS)-4-hydroxy-4-methyl-trans-1-octen-1-yl)-oxycyclopent-1α-yl]heptanoate, comprising an ammonio methacrylate copolymer which mitigates the above drawbacks.

A further object of the present invention is to provide a stable solid dispersion of Misoprostol, (±) methyl 7-[3(α)-hydroxy-2-β-(4(RS)-4-hydroxy-4-methyl-trans-1-octen-1-yl)-oxycyclopent-1α-yl]heptanoate, which is sustained release and can be used as a long term dosage.

It is still another object of the present invention to provide a method of preparing a stable solid dispersion of prostaglandin drug, particularly Misoprostol, (±) methyl 7-[3(α)-hydroxy-2-β-(4(RS)-4-hydroxy-4-methyl-trans-1-octen-1-yl)-oxycyclopent-1α-yl]heptanoate, by using a solvent stripping technology.

These and other objects, advantages and features of the present invention will be more fully understood and appreciated by reference to the written specification and appended drawings.

BRIEF DESCRIPTION OF THE DRAWINGS

The present invention will be further explained with reference to the annexed drawings, wherein.

DETAILED DESCRIPTION OF THE INVENTION

Figure 1:
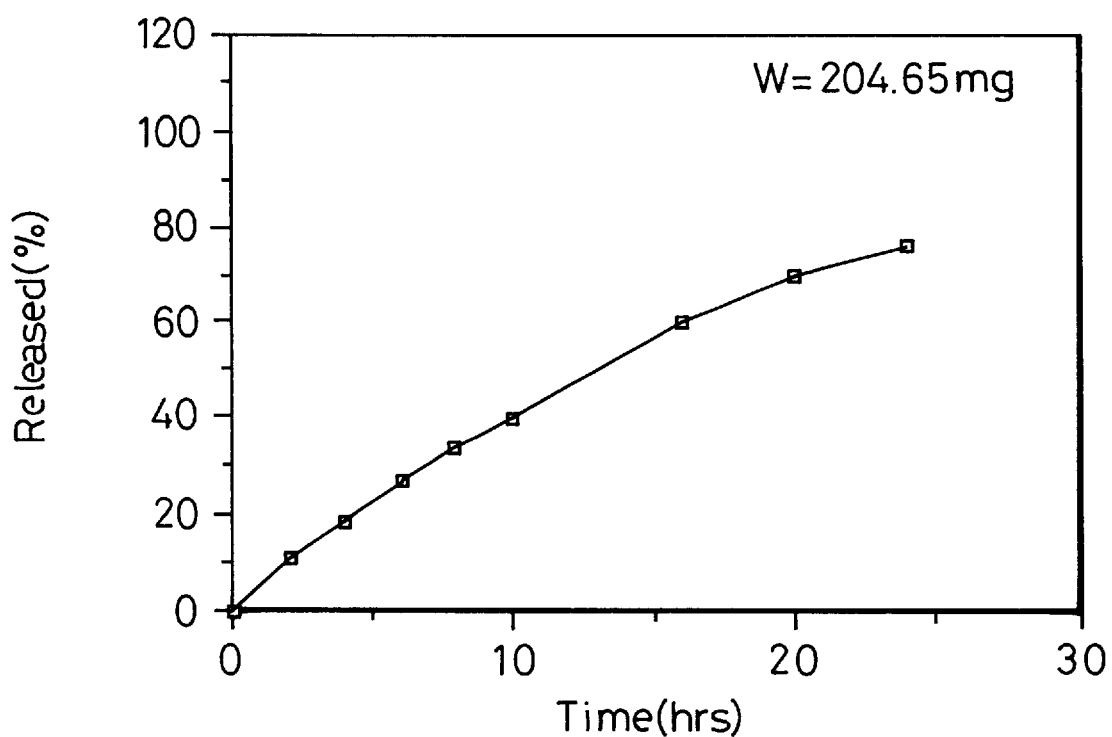
FIG. 1 is a dissolution profile of the sustained release solid dispersion of Misoprostol of Example 7.

The present invention provides a stable solid dispersion of a prostaglandin drug comprising from about 1 to about 1000 parts of an ammonio methacrylate copolymer, based on 1 part of prostaglandin drug. Preferably, the stable solid dispersion of prostaglandin drug of the present invention comprises from about 10 to about 450 parts of the ammonio methacrylate copolymer, based on 1 part of prostaglandin drug. The stable solid dispersion is a sustained release type.

The prostaglandin drug is such as, Misoprostol, (±) methyl 7-[3(α)-hydroxy-2-β-(4(RS)-4-hydroxy-4-methyl-trans-1-octen-1-yl)-oxycyclopent-1-yl]heptanoate. Misoprostol, as known in the art, has the molecular weight of 382.5 and four isomers. U.S. Pat. No. 3,965,143 directed to the Misoprostol is incorporated herein for reference in its entirety. Furthermore, the present invention is capable of stabilizing any pharmaceutically active compounds, particularly those of which the properties are similar to that of Misoprostol.

According to the present invention, the ammonio methacrylate copolymer is selected from the group consisting of Eudragit RS (ammonio methacrylate copolymer, Type B, USP) series, Eudragit RL (ammonio methacrylate copolymer, Type A, USP) series, and the mixture thereof. It should be understood that the ammonio methacrylate copolymer used in the present invention is not limited to the Eudragit RS series and the Eudragit RL series.

Eudragit RS is a tripolymer of ethyl acrylate, methyl methacrylate, and trimethylammonioethyl methacrylate chloride of which the molar proportion of the monomer units is at a ratio of 1:2:0.1 and has a mean molecular weight about 150,000. Furthermore, the Eudragit RS could have any molar ratio of an ammonium group to the remaining neutral (meth)acrylic acid ester group. Preferably, the Eudragit RS has a molar ratio of an ammonium group to a (meth)acrylic acid ester group of 1:40. The Eudragit RS in the present invention is selected from the group consisting of Eudragit RSPM, Eudragit RSPO, Eudragit RS100, Eudragit RS12.5, and the mixture thereof. The wording "Eudragit RSPM" represents general ungrounded powders of Eudragit RS, the wording "Eudragit RSPO" represents grounded fine powders of Eudragit RS, and the wording "Eudragit RS100" represents granules of Eudragit RS, while the wording "Eudragit RS12.5" represents Eudragit RS solution products of which Eudragit RS is dissolved in an organic solvent.

Similarly, Eudragit RL is a tripolymer of ethyl acrylate, methyl methacrylate, trimethylammonioethyl methacrylate chloride of which the molar proportion of the monomer units is at a ratio of 1:2:0.2 and has a mean molecular weight about 150,000. The Eudragit RL could also have any molar ratio of an ammonium group to the remaining neutral (meth)acrylic acid ester group. Preferably, the Eudragit RL has a molar ratio of an ammonium group to a (meth)acrylic acid ester group of 1:20. Furthermore, the Eudragit RL in the present invention is selected from the group consisting of Eudragit RLPM, Eudragit RLPO, Eudragit RL100, Eudragit RL12.5, and the mixture thereof. The wordings "PM," "PO," "100," and "12.5" are defined as above. The mixture of the Eudragit RS series and the Eudragit RL series at any ratio is also used as the ammonio methacrylate copolymer of the present invention.

In accordance with the present invention, the ammonio methacrylate copolymer used in the stable solid dispersion of prostaglandin drug may be selected from the group consisting of Eudragit S (methacrylic acid copolymer, Type B, USP), Eudragit L (methacrylic acid copolymer, Type A, USP), and the mixture thereof.

Eudragit S is a copolymer of methacrylic acid and methyl methacrylate of which the molar proportion of the monomer units is at a ratio of 1:2 and has a mean molecular weight about 135,000. Eudragit L is a copolymer of methacrylic acid and methyl methacrylate of which the molar proportion of the monomer units is at a ratio of 1:1 and also has a mean molecular weight about 135,000. The mixture of the Eudragit S and the Eudragit R at any ratio is also used as the ammonio methacrylate copolymer of the present invention.

The present invention also provides a method of preparing a stable solid dispersion of prostaglandin drug comprising the following steps:

(1) dissolving a prostaglandin drug in a solvent to form a solution;

(2) adding an ammonio methacrylate copolymer into the solution to form a mixture and stirring the mixture for a period of time;

(3) flash evaporating the solvent and blow-drying a residue after evaporation to obtain a solid dispersion;

(4) drying the solid dispersion; and (5) grinding and sieving the solid dispersion to obtain a resultant product.

The prostaglandin drug is such as, Misoprostol, (±) methyl 7-[3(α)-hydroxy-2-β-(4(RS)-4-hydroxy-4-methyl-trans-1-octen-1-yl)-oxycyclopent-1α-yl]heptanoate. Further, the method of the present invention is capable of stabilizing any pharmaceutically active compounds, particularly those of which the properties are similar to that of Misoprostol.

The solvent used in step (1) can be those known in the art and used in any suitable amount. The solvent suitable for use in the preparation of the solid dispersion of the present invention includes ethanol, such as ethanol 200 proof grade, ethanol 3A grade, ethanol USP, ethanol absolute GR, and the mixture thereof; and dichloromethane, such as dichloromethane AR grade; and the mixture of ethanol and dichloromethane at any ratio. The preferred solvent is ethanol absolute GR.

The ammonio methacrylate copolymer used in the method of preparing a stable solid dispersion of prostaglandin drug in the present invention is in the range of from about 1 to about 1000 parts, preferably from about 10 to about 450 parts, based on 1 part of prostaglandin drug. The stable solid dispersion obtained from the method of the present invention is a sustained release type.

According to the preparation method of the present invention, the ammonio methacrylate copolymer used is selected from the group consisting of Eudragit RS (ammonio methacrylate copolymer, Type B, USP), Eudragit RL (ammonio methacrylate copolymer, Type A, USP), and the mixture thereof. Furthermore, the ammonio methacrylate copolymer may be selected from the group consisting of Eudragit S (methacrylic acid copolymer, Type B, USP), Eudragit L (methacrylic acid copolymer, Type A, USP), and the mixture thereof. Further detailed explanations and definitions about the Eudragit RS, Eudragit RL, Eudragit S, and Eudragit L are stated above.

In accordance with the present invention, the mixture in step (2) is stirred for about 1 hour to 3 hours, preferably for about 2 hours. The stirring is conducted under covering. Nitrogen or any other suitable gases can be used to blow-dry the residue in step (3). In step (4) of the present method, the solid dispersion is dried at a temperature of from 40° C. to 50° C. for from about 1 hour to 3 hours.

The resultant solid dispersion product is then stored at a temperature of from about −80° C. to 30° C., preferably from about −27° C. to 5° C. in an air tight container, with the protection of dry silica gel desicators, prior to use.

Further, the present invention provides a method of preparing a stable solid dispersion of prostaglandin drug Misoprostol, (±) methyl 7-[3(α)-hydroxy-2-β-(4(RS)-4-hydroxy-4-methyl-trans-1-octen-1-yl)-oxycyclopent-1-yl]heptanoate, comprising the following steps:

(1) dissolving Misoprostol in a solvent to form a solution;

(2) adding an ammonio methacrylate copolymer into the solution to form a mixture and stirring the mixture for a period of time;

(3) flash evaporating the solvent and blow-drying a residue after evaporation to obtain a solid dispersion;

(4) drying the solid dispersion; and (5) grinding and sieving the solid dispersion to obtain a resultant product.

The ammonio methacrylate copolymer used in the method of preparing a stable solid dispersion of Misoprostol in the present invention is in the range of from about 1 to about 1000 parts, preferably from about 10 to about 450 parts, based on 1 part of Misoprostol.

The solid dispersion of the present invention can be used directly as a powder form, or can be filled in capsules with or without pharmaceutical excipients, or can be compressed into tablets with or without additional excipients, or can be used to coat on an inert or active core to form pellets.

The following examples are offered by way of illustration. The examples are not intended to limit the scope of the invention in any respect and should not be so construed.

EXAMPLES

Example 1

This example is to prepare a stabilized, sustained release solid dispersion of Misoprostol, (±) methyl 7-[3(α)-hydroxy-2-β-(4(RS)-4-hydroxy-4-methyl-trans-1-octen-1-yl)-oxycyclopent-1α-yl]heptanoate, comprising Misoprostol and Eudragit RS (ammonio methacrylate copolymer, Type B, USP) at a ratio of 1:150.

66.7 mg of Misoprostol was dissolved in 47 ml of absolute ethanol. 20 g of Eudragit RS was added into the Misoprostol-ethanol solution to form a mixture of Misoprostol and Eudragit at a ratio of 1:150. The combined Misoprostol-Eudragit-ethanol solution mixture was stirred for 2 hours under covering. Then the solvent was flash evaporated and the residue was blow-dried with Nitrogen. The solid residue, i.e. the solid dispersion, was dried for 2 hours at 40° C. and subsequently the solid residue was ground, sieved through 40 mesh screen. The obtained powder form of the solid dispersion of Misoprostol and Eudragit RS should be stored in an air tight container.

Example 2

The steps of Example 1 were repeated, except that 40 g and 60 g of Eudragit RS were added into the Misoprostol-ethanol solution to form a stabilized, sustained release solid dispersion of Misoprostol and Eudragit at a ratio of 1:300 and 1:450, respectively.

Example 3

The steps of Example 1 were repeated, except that 47 ml of a solvent containing 9 parts of absolute ethanol and 1 part of dichloromethane, and 40 g of Eudragit RS were used to form a stabilized, sustained release solid dispersion of Misoprostol and Eudragit at a ratio of 1:300.

Example 4

The steps of Example 1 were repeated, except that 47 ml of dichloromethane and 40 g of Eudragit RS were used to form a stabilized, sustained release solid dispersion of Misoprostol and Eudragit at a ratio of 1:300.

Example 5

The steps of Example 1 were repeated, except that three different amounts, i.e. 1.33 g, 2.67 g and 5.34 g of Eudragit RS were used to form three stabilized, sustained release solid dispersions of Misoprostol and Eudragit at a ratio of 1:10, 1:20 and 1:40, respectively. After the solid residues, i.e., the solid dispersions were dried for about 2 hours at 40° C., the solid residues were ground and sieved through 100 mesh. The fine powder form of these solid dispersions were stored at a temperature of −27° C. in an air tight container with the protection of dry silica gel desiccators, prior to use.

Example 6

The steps of Example 5 were repeated, except that two different amounts, i.e., 6.67 g and 60 g of Eudragit RL were used to form a stabilized, sustained release solid dispersion of Misoprostol and Eudragit at a ratio of 1:50 and 1:450, respectively.

Example 7

The steps of Example 5 were repeated, except that 6.67 g of Eudragit RS was used to form a stabilized, sustained release solid dispersion of Misoprostol and Eudragit at a ratio of 1:50.

Example 8

The sustained release solid dispersion of Misoprostol and Eudragit at a ratio of 1:50 obtained from Example 7 was used to prepare homogenous powder blends.

Seven homogenous powder blends were prepared by mixing the solid dispersion obtained from Example 7 with seven individual different pharmaceutical excipients at a ratio by weight as follows. One part of the sustained release solid dispersion was mixed with five parts of Avicel pH 102 (Microcrystalline cellulose), Eudragit RS, Corn Starch and Mannitol, respectively. Furthermore, fifty parts of the sustained release solid dispersion was mixed with two parts of Talc, Magnesium Stearate and Hydrogenated Castor Oil, respectively.

Example 9

The sustained release solid dispersion of Misoprostol and Eudragit at a ratio of 1:50 obtained from Example 7 was used to prepare filled sustained release capsules.

20.4 mg of the solid dispersion obtained from Example 7 was weighed and filled into No. 2 gelatin capsules. Each sustained release capsule contained 400 μg of prostaglandin drug, Misoprostol.

Example 10

The sustained release solid dispersion of Misoprostol and Eudragit at a ratio of 1:50 obtained from Example 7 was used to prepare sustained release tablets.

20.4 mg of the solid dispersion obtained from Example 7, 167.6 mg of Avicel pH 102 (microcrystalline cellulose), 10.0 mg of sodium starch glycolate, and 2.0 mg of hydrogenated castor oil were mixed to prepare one sustained release tablet. The total weight of each sustained release tablet was 200 mg. Totally 2000 sustained release tablets were prepared. Each sustained release tablet contained 400 μg of prostaglandin drug, Misoprostol.

Example 11

The stability of Misoprostol in the solid dispersion of Examples 1 to 10 was determined after storing at various temperatures for different time periods. After assaying the percent potency remained of Misoprostol in each sample by high performance liquid chromatography (HPLC), the results were summarized in Table I for Examples 1–4, Table II for Examples 5 and 6, Table III for Example 8, and Table IV for Examples 7, 9 and 10, for a predetermined period at each temperature. All assay was done by using a Spectra-Physics Liquid Chromatography equipped with Model P2000 pump, AS 3000 autosampler, UV 1000 detector, IMS 1000 integrator and SN 4000 controller. The wave length of detector was set at 210 nm with a chart speed of 0.5 cm/min. Assay was achieved by using a Lichrospher 100, RP-8, 125×4 mm ID column, eluted with a mobile phase containing 45 parts of acetonitrile and 55 parts of pH 2.81 phosphate buffer in volume with a flow rate of 1 ml/minute.

TABLE I

Stability Data on Misoprostol Alone and Its Eudragit Solid Dispersions (% Potency Remained)

| Storage Temperature | 5° C. | | | 30° C. | | 50° C. | | | 70° C. |
|---|---|---|---|---|---|---|---|---|---|
| Storage Time (Week) | 0 | 3 | 6 | 3 | 6 | 1 | 3 | 6 | 1 |
| Misoprotol Alone | 100 | 100 | 94 | 92.2 | 82.7 | 93.9 | 91.7 | 64 | 81.2 |
| Ex. 1 (1:150 Ratio) | 100 | 99.2 | 99.5 | 95.8 | 97.7 | 97.1 | 91.4 | 80.1 | 89.8 |
| Ex. 2 (1:300 Ratio) | 100 | 99.2 | 98.6 | 94.2 | 95.8 | 95.6 | 90.7 | 81.5 | 88.5 |
| Ex. 2 (1:450 Ratio) | 100 | 100 | 100 | 100 | 100 | 100 | 93 | 83.3 | 83 |
| Ex. 3 (1:300 Ratio) | 100 | 100 | 100 | 100 | 100 | 99.7 | 95.3 | 95.8 | 92.4 |
| Ex. 4 (1:300 Ratio) | 100 | 100 | 99.7 | 100 | 100 | 99.5 | 96.1 | 91.7 | 85.9 |

TABLE II

Stability Data on Misoprostol Alone and Its Eudragit Solid Dispersions (% Potency Remained)

| Storage Temperature | 30° C. | | | | 50° C. | | | | 70° C. | |
|---|---|---|---|---|---|---|---|---|---|---|
| Storage Time (Week) | 0 | 3 | 6 | 12 | 1 | 3 | 6 | 12 | 1 | 2 |
| Misoprostol Alone | 100 | 92.2 | 82.7 | 14.4 | 93.9 | 91.7 | 64 | 10.9 | 81.2 | 41.5 |
| Ex. 5 (1:10 Ratio) | 100 | 99.5 | 102.2 | 93.0 | 97.0 | 97.2 | 94.8 | 91.8 | — | — |
| Ex. 5 (1:20 Ratio) | 100 | 99.1 | 98.1 | 95.6 | 102 | 95.8 | 95.0 | 93.7 | 93.9 | 88.6 |
| Ex. 5 (1:40 Ratio) | 100 | 98.8 | 100.4 | 97.5 | 100.7 | 99.7 | 98.3 | 96.5 | 95.0 | 92.3 |
| Ex. 6 (1:50 Ratio) | 100 | 96.5 | 94.5 | 96.6 | 96.5 | 97.0 | 93.0 | 93.0 | 94.5 | 90.5 |
| Ex. 6 (1:450 Ratio) | 100 | 102.9 | 101.5 | 97 | 97.9 | 95.3 | 95.2 | 95.7 | 97.6 | 92.3 |

TABLE III-1

Stability Data of Misoprostol in Eudragit Solid Dispersions When Mixed with Seven Different Pharmaceutical Excipients in Ex. 8 (% Potency Remained)

| | (Solid Dispersion:Excipients = 1:5) | | | |
|---|---|---|---|---|
| Ratio Excipients | Avicel pH102 | Eudragit RS | Corn Starch | Mannitol |
| After 1 week at 70° C. Storage | 102.6 | 97.7 | 100.6 | 97.3 |

TABLE III-2

Stability Data of Misoprostol in Eudragit Solid Dispersions When Mixed with Seven Different Pharmaceutical Excipients in Ex. 8 (% Potency Remained)

| | (Solid Dispersion:Excipients 50:2) | | |
|---|---|---|---|
| Ratio Excipients | Talc | Magnesium Stearate | Hydrogenated Castor Oil |
| After 1 week at 70° C. Storage | 98.4 | 99.9 | 100.0 |

TABLE IV

Stability Data of Misoprostol on Its Sustained Release Solid Dispersion at 1:50 Ratio in Ex. 7, Its Sustained Release Tablets in Ex. 10, and Its Sustained Release Capsules in Ex. 9 (% Potency Remained)*

| Storage Relative Humidity (RH) and Temperature | 75% RH +37° C. | | | 75% RH +43° C. | | | 75% RH +50° C. | | |
|---|---|---|---|---|---|---|---|---|---|
| Storage Time (Month) | 1 | 3 | 6 | 1 | 3 | 6 | 1 | 3 | 6 |
| Misoprostol-Eudragit Solid Dispersion (1:50 Ratio) | 95.1 | 95.9 | 92.1 | 96.0 | 94.7 | 90.1 | 93.5 | 90.7 | 76 |
| Sustained Release Tablets | 100.0 | 96.6 | 97.3 | 100.0 | 96.4 | 91.6 | 93.8 | 89.6 | 56.8 |
| Sustained Release Capsules | 97.9 | — | 95.4 | 95.3 | — | 92.2 | 92.8 | — | 68.8 |

*An air tight polyethylene container was used for this stability study.

The stability of the solid dispersion of Misoprostol of the present invention, and the capsules and the tablets prepared therefrom is tested after storing at various temperatures for different time periods. It is found that the present invention is capable of providing a stabilized, solid dispersion of Misoprostol, (±) methyl 7-[3(α)-hydroxy-2-β-(4(RS)-4-hydroxy-4-methyl-trans-1-octen-1-yl)-oxycyclopent-1α-yl] heptanoate. Furthermore, according to the present invention, the capsules filled with the stabilized, solid dispersion of Misoprostol or the tablets compressed from the stabilized solid dispersion of Misoprostol are stable and sustained release type.

Example 12

The sustained release dissolution profile of Misoprostol-Eudragit solid dispersion at the ratio of 1:50 obtained from Example 7 and its sustained release tablets obtained from Example 10 were generated by using a USP paddle dissolution tester at 37° C. with an agitation speed of 75 rpm. The sustained release dissolution profile were shown in FIGS. 1 (Example 7) and 2 (Example 10). Specifically, the dissolution testing in FIG. 1 was conducted in 0.2% sodium lauryl sulfate (SLS) dissolution medium.

At each time point, dissolution samples were assayed by the high performance liquid chromatography (HPLC) method described in Example 11. A typical dissolution profile of a commercial available Misoprostol immediate release tablet, known as Cytotec which contains 0.2 mg Misoprostol, was shown on FIG. 3 for the purpose of comparison.

Figure 2:
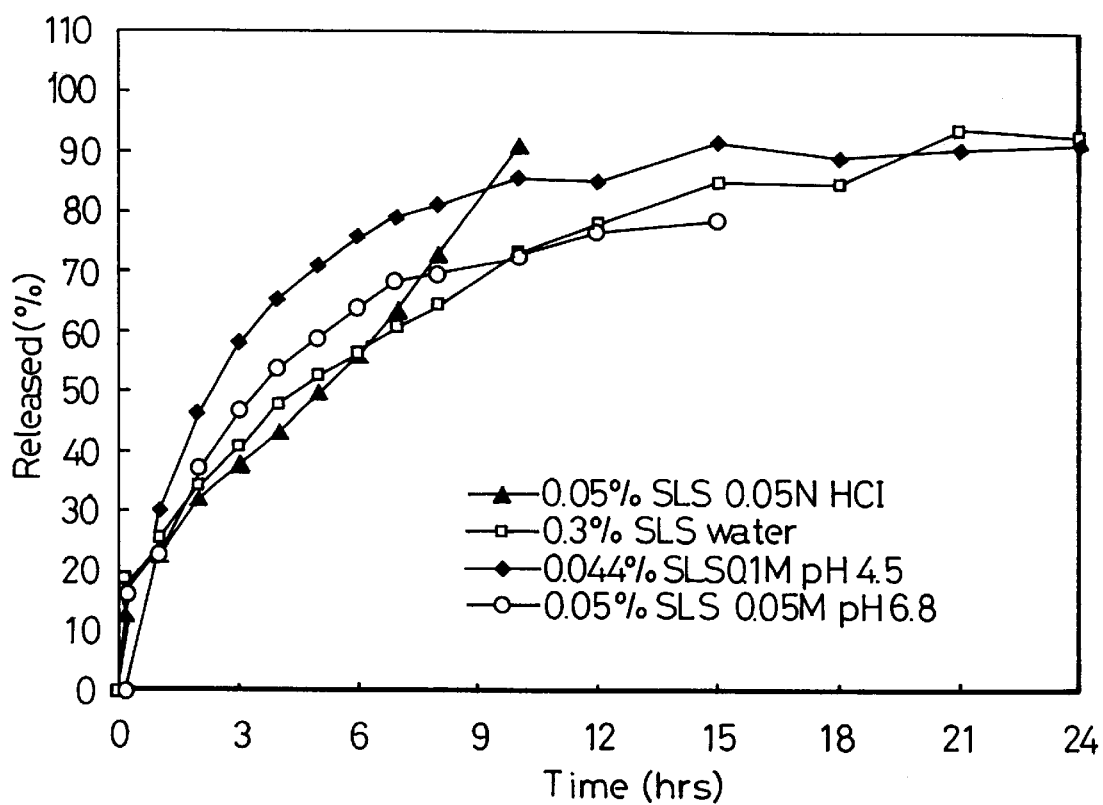
FIG. 2 is a dissolution profile of the sustained release Misoprostol tablets of Example 10.
Figure 3:
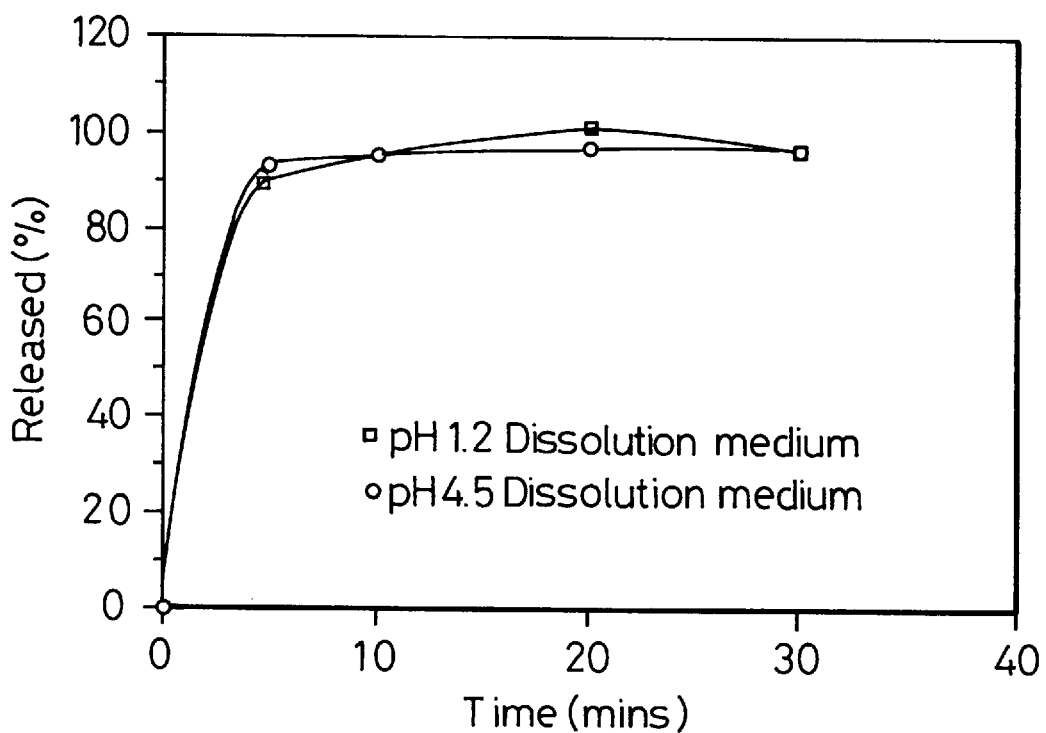
FIG. 3 is a dissolution profile of a commercial available Misoprostol immediate release tablet.

From FIGS. 1, 2 and 3, it is clear that the sustained release effect of the solid dispersion of Misoprostol of the present invention is better than that of commercial available, Misoprostol immediate release tablet. In accordance with the present invention, only one tablet or capsule produced from the solid dispersion of Misoprostol might be all it needed in one day since the solid dispersion of Misoprostol is sustained release type.

While the invention has been described with respect to certain preferred exemplifications and embodiments, it is not intended to limit the scope of the invention thereby, but solely by the claims appended hereto.

We claim:

1. A stable solid dispersion of Misoprostol in powder form comprising from about 1 to about 1000 parts of an ammonio methacrylate copolymer and about 1 part of Misoprostol, (±)methyl 7-[3(α)-hydroxy-2-β-(4(RS)-4-hydroxy-4-methyl-trans-1-octen-1-yl)-oxycyclopent-1α-yl]heptanoate.

2. A stable solid dispersion according to claim 1, comprising from about 10 to about 450 parts of the ammonio methacrylate copolymer.

3. A stable solid dispersion according to claim 1 being a sustained release solid dispersion.

4. A stable solid dispersion according to claim 1, wherein the ammonio methacrylate copolymer is selected from the group consisting of ammonio methacrylate copolymer, Type B (Eudragit RS), ammonio methacrylate copolymer, Type A (Eudragit RL), and mixtures thereof.

5. A solid dispersion according to claim 4, wherein the ammonio methacrylate copolymer, Type B (Eudragit RS) is selected from the group consisting of powders of ammonio methacrylate copolymer, Type B (Eudragit RSPM), fine powders of ammonio methacrylate copolymer, Type B (Eudragit RSPO), granules of ammonio methacrylate copolymer, Type B (Eudragit RS100), ammonio methacrylate copolymer, Type B dissolved in an organic solvent (Eudragit RS12.5), and mixtures thereof.

6. A solid dispersion according to claim 4, wherein the ammonio methacrylate copolymer, Type B (Eudragit RS)

has any molar ratio of ammonium groups to (meth)acrylic acid ester groups.

7. A solid dispersion according to claim 4, wherein the ammonio methacrylate copolymer, Type B (Eudragit RS) has a molar ratio of ammonium groups to (meth)acrylic acid ester groups of 1:40.

8. A solid dispersion according to claim 4, wherein the ammonio methacrylate copolymer, Type A (Eudragit RL) is selected from the group consisting of powders of ammonio methacrylate copolymer, Type A (Eudragit RLPM), fine powders of ammonio methacrylate copolymer, Type A (Eudragit RLPO), granules of ammonio methacrylate copolymer, Type A (Eudragit RL100), ammonio methacrylate copolymer, Type A dissolved in an organic solvent (RL12.5), and mixtures thereof.

9. A solid dispersion according to claim 4, wherein the ammonio methacrylate copolymer, Type A (Eudragit RL) has any molar ratio of ammonium groups to (meth)acrylic acid ester groups.

10. A solid dispersion according to claim 4, wherein the ammonio methacrylate copolymer, Type A (Eudragit RL) has a molar ratio of ammonium groups to (meth)acrylic acid ester groups of 1:20.

11. A solid dispersion according to claim 1, wherein the ammonio methacrylate copolymer is selected from the group consisting of methacrylic acid copolymer, Type B (Eudragit S), methacrylic acid copolymer, Type A (Eudragit L), and mixtures thereof.

12. A method of preparing a stable solid dispersion of Misoprostol in powder form comprising:

(1) dissolving Misoprostol in a solvent to form a solution;

(2) adding an ammonio methacrylate copolymer into the solution to form a mixture and stirring the mixture for a period of time, wherein the ammonio methacrylate copolymer is added in an amount of from about 10 to about 450 parts based on 1 part of Misoprostol;

(3) flash evaporating the solvent and blow-drying a residue after evaporation to obtain a solid dispersion;

(4) drying the solid dispersion; and (5) grinding and sieving the solid dispersion.

13. A method according to claim 12, wherein the solvent is selected from the group consisting of ethanol, dichloromethane, and the mixture thereof.

14. A method according to claim 13, wherein the ethanol is selected from the group consisting of ethanol 200 proof grade, ethanol 3A grade, ethanol USP, ethanol absolute GR, and the mixtures thereof.

15. A method according to claim 12, wherein the solvent is ethanol absolute GR.

16. A method according to claim 13, wherein the dichloromethane is dichloromethane AR grade.

17. A method according to claim 12, wherein the ammonio methacrylate copolymer is selected from the group consisting of ammonio methacrylate copolymer, Type B (Eudragit RS), ammonio methacrylate copolymer, Type A (Eudragit RL), and mixtures thereof.

18. A method according to claim 17, wherein the ammonio methacrylate copolymer, Type B, (Eudragit RS) is selected from the group consisting of powders of ammonio methacrylate copolymer, Type B (Eudragit RSPM), fine powders of ammonio methacrylate copolymer, Type B (Eudragit RSPO), granules of ammonio methacrylate copolymer, Type B (Eudragit RS100), ammonio methacrylate copolymer, Type B dissolved in an organic solvent (Eudragit RS12.5), and mixtures thereof.

19. A method according to claim 17, wherein the ammonio methacrylate copolymer, Type A (Eudragit RL) is selected from the group consisting of powders of ammonio methacrylate copolymer, Type A (Eudragit RLPM), fine powders of ammonio methacrylate copolymer, Type A (Eudragit RLPO), granules of ammonio methacrylate copolymer, Type A (Eudragit RL100), ammonio methacrylate copolymer, Type A dissolved in an organic solvent (Eudragit RL12.5), and mixtures thereof.

20. A method according to claim 12, wherein the ammonio methacrylate copolymer is selected from the group consisting of methacrylic acid copolymer, Type B (Eudragit S), methacrylic acid copolymer, Type A (Eudragit L), and mixtures thereof.

21. A method according to claim 12, wherein the mixture in step (2) is stirred for about 1 hour to about 3 hours.

22. A method according to claim 21, wherein the mixture in step (2) is stirred for about 2 hours.

23. A method according to claim 12, wherein the solid dispersion is dried at a temperature of from 40° C. to 50° C.

24. A method according to claim 12, wherein the solid dispersion is dried for from about 1 hour to about 3 hours.

* * * * *

UNITED STATES PATENT AND TRADEMARK OFFICE
CERTIFICATE OF CORRECTION

PATENT NO. : 5,889,051
DATED : March 30, 1999
INVENTOR(S) : David Chen et al.

It is certified that error appears in the above-indentified patent and that said Letters Patent is hereby corrected as shown below:

Claim 12, Col. 9, line 35, after "parts", insert --,--.

Claim 14, Col. 10, line 4, before "mixtures", delete "the".

Signed and Sealed this

Twenty-first Day of December, 1999

Attest:

Q. TODD DICKINSON

Attesting Officer

Acting Commissioner of Patents and Trademarks